United States Patent [19]

Epstein et al.

[11] 4,165,250

[45] Aug. 21, 1979

[54] RIBOFLAVIN PURIFICATION

[75] Inventors: Albert Epstein, Edison; Glen Graham, Rocky Hill; William A. Sklarz, Edison, all of N.J.

[73] Assignee: Merck & Co., Inc., Rahway, N.J.

[21] Appl. No.: 850,991

[22] Filed: Nov. 14, 1977

Related U.S. Application Data

[63] Continuation-in-part of Ser. No. 669,139, Mar. 22, 1976, abandoned, which is a continuation-in-part of Ser. No. 609,132, Aug. 29, 1975, abandoned.

[51] Int. Cl.$^2$ .............................................. C12D 5/04
[52] U.S. Cl. .................................. 435/267; 426/479; 435/66
[58] Field of Search .......... 195/2, 4, 35, 42, DIG. 10; 426/431, 479

[56] References Cited

U.S. PATENT DOCUMENTS

| | | | |
|---|---|---|---|
| 2,387,023 | 10/1945 | Hines | 195/42 |
| 2,445,128 | 7/1948 | Tanner et al. | 195/28 |
| 2,483,855 | 10/1949 | Stiles | 195/35 |
| 2,571,896 | 10/1951 | Keresztesy et al. | 260/211.3 |
| 2,797,215 | 6/1957 | Dale | 260/211.3 |
| 2,807,611 | 9/1957 | Howe | 260/211.3 |
| 3,576,719 | 4/1971 | Murao | 195/2 |

*Primary Examiner*—Alvin E. Tanenholtz
*Attorney, Agent, or Firm*—Donald J. Perrella; Julian S. Levitt

[57] ABSTRACT

Riboflavin is recovered from fermentation broth by diluting the broth with a predetermined quantity of water, centrifuging the diluted broth to form a sludge, resuspending the sludge with a predetermined quantity of water, and centrifuging the resuspended sludge to yield a product usable directly as an animal feed supplement or suitable for further purification for pharmaceutical use. Optionally the broth or resuspended sludge is treated with an enzyme before centrifugation.

6 Claims, No Drawings

RIBOFLAVIN PURIFICATION

RELATED APPLICATION

This application is a continuation-in-part of copending application Ser. No. 669,139 filed Mar. 22, 1976, now abandoned, which in turn was a continuation-in-part of copending application Ser. No. 609,132 filed Aug. 29, 1975, now abandoned.

BACKGROUND OF THE INVENTION

This invention relates to the purification of riboflavin and, more particularly, it relates to a process wherein riboflavin fermentation solids are upgraded to a product directly usable as an animal feed supplement or adaptable for further purification for pharmaceutical use.

The preparation of riboflavin (vitamin $B_2$) by fermentation methods is known in the art as is shown, for example, by U.S. Pat. Nos. 2,387,023, 2,445,128, 2,483,855 and 2,571,896. Conventional methods of isolating fermentation produced riboflavin, however, yield a low purity riboflavin which must be upgraded before it is suitable even as an animal feed supplement. The treatment to upgrade the riboflavin is not only time consuming and costly but often involves conditions under which riboflavin is unstable, and gives rise to waste products which are not readily biodegradable.

It is, accordingly, an object of the present invention to provide an improved process for recovering riboflavin. Another object is to provide a process wherein riboflavin fermentation broth or riboflavin fermentation solids are upgraded to an intermediate product either usable as such as an animal feed supplement or suitable for further purification for pharmaceutical use. A further object is to provide an economical process which maximizes riboflavin recovery. These and other objects of the present invention will be apparent from the following description.

SUMMARY OF THE INVENTION

Riboflavin is recovered from fermentation broth by diluting the broth with a predetermined quantity of water, centrifuging the diluted broth to form a sludge, resuspending the sludge with a predetermined quantity of water, and centrifuging the resuspended sludge to yield a product usable directly as an animal feed supplement or suitable for further purification for pharmaceutical use. Optionally the broth and resuspended sludge are treated with an enzyme before centrifugation. Optionally, but preferably, the broth and sludge are treated with a proteolytic enzyme before centrifugation.

DETAILED DESCRIPTION

The starting material for the present invention is a riboflavin fermentation broth. The preparation of riboflavin from a fermentation broth is known and is described, for example, in the U.S. patents previously mentioned whose disclosures are hereby incorporated by reference. Briefly, a nutrient medium is sterilized and inoculated with an organism capable of producing riboflavin. When the fermentation yield approaches or is at about the maximum the broth is heated to a temperature of from about 50° C. to about 65° C. for from about 15 to about 45 minutes, preferably for from about 25 to about 35 minutes and the riboflavin recovery begins. This heating serves to lyse the cells and to decrease broth viscosity thus enhancing the effectiveness of subsequent recovery and purification steps. Heating beyond about 45 minutes is undesirable as it increases rather than decreases broth viscosity.

The broth is then cooled and diluted with a predetermined quantity of water. The quantity of water chosen is insufficient to dissolve suspended solids in the broth but sufficient to optimize centrifugal separation by both diluting the previously dissolved solids in the broth and enhancing separation of solid suspended particles having a density less than that of crystalline riboflavin. Typically this added quantity of water is from about 25 to about 100 volume % of the volume of the fermentation broth, and preferably is from about ⅓ to about ½ the volume of the fermentation broth.

A proteolytic enzyme may be present during the heating or may be added following the heating. The enzyme is allowed to digest proteinaceous matter for several hours, generally for from about 1 to about 5 hours, preferably for from about 3 to about 4 hours. During enzyme treatment the pH is adjusted to a level at which the enzyme functions most effectively, generally at a pH of from about 6.0 to about 9.0. The broth is then cooled, and the pH, if alkaline, is adjusted to about pH 7.0.

The diluted broth either with or without enzyme treatment next is converted to a sludge by centrifugation. The sludge is then resuspended with a predetermined quantity of water. The quantity of water chosen is insufficient to dissolve suspended solids in the resuspended sludge but sufficient to optimize separation of solid particles having a density less than that of crystalline riboflavin. Typically this quantity of water is equal to from about 1 volume to about 3 volumes per volume of sludge, and preferably is about twice the volume of the sludge. On a solids basis, the resuspended sludge contains from about 15 to about 30 weight % solids. The resuspended sludge is then centrifuged to yield a centrifugate usable as such as a animal feed supplement.

Examples of enzymes suitable for use in carrying out the present invention are alkaline proteases such as B. subtilis protease, B. ligninoformis protease, and B. amylofaciens protease, or neutral proteases such as neutral B. subtilis proteases. Such enzymes are commercially available, for example, a suitable alkaline protease enzyme is Rhozyme P-62 supplied by Rohm and Haas Co. and a suitable neutral protease enzyme is Enzeco Bacterial Protease supplied by Enzyme Development Corp.

The following examples illustrate the present invention without, however, limiting the same thereto. Unless indicated otherwise, all temperatures are expressed in degrees Celsius.

EXAMPLE 1

One liter of riboflavin fermentation broth is heated to 60° for 30 minutes after completion of fermentation. The broth is then cooled to 25°, and diluted to 1.4 liters with distilled water. The diluted broth is centrifuged and the centrifugate is resuspended in two volumes of water and centrifuged again. The purity of the resulting centrifugate is three times greater than untreated dried fermentation broth and is of sufficient purity to permit its use as an animal feed supplement without further treatment.

EXAMPLE 2

One liter of riboflavin fermentation broth is heated to 60° after completion of fermentation a 0.068 gram aliquot of B. subtilis alkaline protease having a 3.65 casein unit activity is then added and allowed to react for 3 hours. One casein unit is defined as the ability of 1 gram of enzyme to solubilize 270 grams of azo-casein in 1 hour at 40° at pH 8.0. Following heating the broth is cooled to 25°, neutralized to pH 7.0 and diluted to 1.4 liters with distilled water. The diluted broth is centrifuged and the centrifugate is resuspended in two volumes of water and centrifuged again. The purify of the resulting centrifugate is 20% greater than in Example 1.

EXAMPLE 3

A sample of riboflavin fermentation broth is processed exactly as in Example 2 but using 0.48 grams of 3.0 Anson unit activity B. ligninoformis alkaline protease instead of B. subtilis alkaline protease. One Anson unit is defined as the number of grams of hemoglobin digested by 1 gram of enzyme in 10 minutes at 25° and pH 10.1 which do not precipitate by trichloroacetic acid addition. The purity of the enzyme treated sludge is 27% greater than non-enzyme treated sludge. The enzyme treated sludge is 3.4 times purer than untreated dried fermentation broth.

The enzyme treatment of the fermentation broth can be carried out simultaneously with a heat sterilization cycle in the fermentation vessel with similar results.

EXAMPLE 4

A 553 ml portion of pasteurized riboflavin fermentation broth is inoculated with 10 ml of B. subtilis (National Collection Type Culture No. 3610) nutrient broth seed culture. The fermentation is allowed to continue 48 hours at 37°. Suspended solids decrease 72% during fermentation. The B. subtilis fermented broth is heated, diluted to 750 ml with water and centrifuged. The centrifugate is suspended with 200 ml water and centrifuged again. The centrifugate is 53% more pure than a non B. subtilis fermented control, and 4.4 times more pure than dried fermentation broth.

EXAMPLE 5

The procedure of Example 1 is repeated except that before centrifuging, the resuspended centrifugate is brought to pH 8.0 and heated to 60°. B. subtilis alkaline protease enzyme, 0.049 g, having an activity of 3.65 casein units is added and allowed to react for a period of 3 hours. The slurry is cooled, neutralized, and centrifuged. The purity of the centrifugate is 41% higher than that of a control sample receiving no enzyme treatment. Equivalent enzyme treatment carried out on the same broth of the same fermentation batch gives only 20% increased purity over controls.

What is claimed is:

1. A process for the recovery of purified riboflavin from a riboflavin and cell containing fermentation broth comprising:
    heating the broth when the fermentation yield is at about the maximum to from about 50° to about 65° C. for from about 15 to about 45 minutes to lyse the cells and decrease beoth viscosity,
    adding to the heated fermentation broth a volume of water insufficient to dissolve suspended solids in said broth but sufficient to optimize separation by both diluting previously dissolved solids and permitting centrifugal separation of solid suspended particles having a density less than that of crystalline riboflavin,
    then centrifuging the treated fermentation broth containing the added quantity of water to produce a sludge,
    resuspending the sludge with a quantity of water insufficient to dissolve suspended solids but sufficient to optimize separation of solid particles having a density less than that of crystalline riboflavin,
    and centrifuging the resuspended sludge to obtain a purified riboflavin-containing centrifugate usable as such as an animal feed supplement.

2. A process according to claim 1 wherein the quantity of water added to the heated fermentation broth is from about 25 volume % to about 100 volume % of the original volume of the fermentation broth.

3. A process according to claim 1 wherein the volume of water added to the heated fermentation broth is equal to from about ⅓ to about ½ of the original volume of the fermentation broth.

4. A process according to claim 1 wherein the volume of water used to resuspend the sludge is from about one to about three times the volume of the sludge.

5. A process according to claim 1 wherein the broth is treated with a proteolytic enzyme during heating or following the heating and before being centrifuged to produce a sludge, the enzyme not affecting riboflavin but being effective either to solubilize proteinaceous material or to convert it to material of reduced density separable by centrifugation.

6. A process according to claim 1 wherein theresuspended sludge is treated with a proteolytic enzyme before being centrifuged.

* * * * *